US00PP37090P2

(12) United States Plant Patent
Bacon et al.

(10) Patent No.: US PP37,090 P2
(45) Date of Patent: Nov. 11, 2025

(54) PLUM TREE NAMED 'SUPLUM65'

(50) Latin Name: *Prunus salicina*
Varietal Denomination: SUPLUM65

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/303,050

(22) Filed: Aug. 18, 2025

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 5/0862
See application file for complete search history.

*Primary Examiner* — Kent L Bell
(74) *Attorney, Agent, or Firm* — Knobbe, Martens, Olson & Bear, LLP

(57) ABSTRACT

The new variety 'SUPLUM65' is characterized by having circular-shaped fruit that is very large sized for an early-season plum, with black-colored skin, firm, red-colored flesh, and a sweet-mild flavor.

1 Drawing Sheet

Latin name of the genus and species claimed: *Prunus salicina.*

Variety denomination: 'SUPLUM65'.

BACKGROUND AND SUMMARY OF THE INVENTION

This application relates to the discovery and asexual propagation of a new and distinct variety of plum tree, *Prunus salicina* 'SUPLUM65'. The new variety was first originated by hybridization near Wasco, Kern County, California and identified in June 2017 by Terry A. Bacon and Terrence J. Frett as breeder number 'PL2077RB'.

The seed parent is 'Suplumfiftyfour' (U.S. Plant Pat. No. 29,766), and the pollen parent is 'PL1396RB' (unpatented). The parent varieties were first crossed in February 2014, the date of first sowing being December 2014 and the date of first flowering being February 2017. The new plum variety 'SUPLUM65' was first asexually propagated by Terry A. Bacon and Terrence J. Frett near Wasco, Kern County, California in February 2018 by dormant grafting.

The new variety 'SUPLUM65' is characterized by having circular-shaped fruit that is very large sized for an early-season plum, with black-colored skin, firm, red-colored flesh, and a sweet-mild flavor.

The new variety 'SUPLUM65' differs from its seed parent 'Suplumfiftyfour' (U.S. Plant Pat. No. 29,766) in that the beginning of bloom is about February 22$^{nd}$ and harvest starts about June 11$^{th}$, compared to February 23$^{rd}$ and July 28$^{th}$, respectively, for 'Suplumfiftyfour'. Additionally, the new variety 'SUPLUM65' has a fruit weight of 165 g, compared to a fruit weight of 200 g for 'Suplumfiftyfour'

The new variety 'SUPLUM65' differs from its pollen parent 'PL1396RB' (unpatented) in that the ripening of the fruit of the new variety starts about June 11$^{th}$, compared to October 2$^{nd}$ for 'PL1396RB'. Additionally, the new variety 'SUPLUM65' has fruit with a weight of 165 g and red-colored flesh, compared to fruit with a weight of 160 g and pink-colored flesh for 'PL1396RB'. Lastly, the fruit of the new variety 'SUPLUM65' has a titratable acidity of 0.70%, compared to 0.057% for 'PL1396RB'.

The fruit of the new variety 'SUPLUM65' has 90 to 100 percent over color like 'Suplumfiftyseven' (U.S. Plant Pat. No. 31,849), but the ripening of the fruit of the new variety 'SUPLUM65' starts 7 days earlier than that of 'Suplumfiftyseven'. Additionally, the new variety 'SUPLUM65' has red flesh, compared to dark-red flesh for 'Suplumfiftyseven'. Further, the new variety 'SUPLUM65' has a fruit weight of 165 g and a fruit Brix of 17, compared to a fruit weight of 130 g and a fruit Brix of 16 for 'Suplumfiftyseven'. Lastly, the fruit of the new variety 'SUPLUM65' has a titratable acidity of 0.70% and Brix:Acid ratio of 24, compared to 0.60% and 27, respectively, for 'Suplumfiftyseven'.

The fruit of the new variety 'SUPLUM65' has 90 to 100 percent over color like 'Suplumfiftyeight' (U.S. Plant Pat. No. 33,247), but the ripening of the fruit of the new variety 'SUPLUM65' starts 5 days later than that of 'Suplumfiftyeight'. Additionally, the new variety 'SUPLUM65' has red flesh compared to dark-red flesh for 'Suplumfiftyeight'. The new variety 'SUPLUM65' has a fruit weight of 165 g and a fruit Brix of 17, compared to a fruit weight of 132 g and a fruit Brix of 18 for 'Suplumfiftyeight'. Lastly, the fruit of new variety 'SUPLUM65' has a titratable acidity of 0.70% and Brix:Acid ratio of 24, compared to 0.55% and 33, respectively, for 'Suplumfiftyeight'.

The new variety 'SUPLUM65' has been shown to maintain its distinguishing characteristics through successive asexual propagations by, for example, cuttings and grafting.

BRIEF DESCRIPTION OF THE PHOTOGRAPH

The accompanying color photographic illustration taken from a six-year-old plant shows typical specimens of the foliage and fruit of the plum variety 'SUPLUM65'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, sixth edition, 2019 reprint.

The descriptive matter which follows pertains to six-year-old 'SUPLUM65' trees grown in the vicinity of Wasco, Kern County, California during 2025 and is believed to apply to plants of the variety grown under similar conditions of soil and climate elsewhere.

TREE

General: (Measurements taken on six-year-old trees unless otherwise noted).

- *Size*.—Medium: reaches a height of approximately 2.5 meters to 3 meters with normal pruning.
- *Habit*.—Upright.
- *Vigor*.—Strong.
- *Productivity*.—Very productive. About 481 cartons (10-1b cartons) per acre. Fruit set is usually two or more times the desired amount for marketable size fruit. Thinning and spacing of fruit is necessary.
- *Fertility*.—Self-incompatible.
- *Hardiness*.—Hardy in all fruit growing areas of California. Winter chilling requirement is approximately 600 hours at or below 7.2° C.
- *Disease resistance/susceptibility*.—Under close observation in Kern County, California, no particular plant/fruit disease resistance/susceptibility has been observed.
- *Insect resistance/susceptibility*.—Under close observation in Kern County, California, no particular plant/fruit insect resistance/susceptibility has been observed.

Trunk: (Measurements taken at approximately 30 cm above soil line on mature tree).

- *Diameter*.—Approximately 9 cm to 10 cm.
- *Texture*.—Medium shaggy, increasing with age of tree.
- *Trunk color*.—About Moderate Olive Brown 199A, becoming darker with age.

Branches: (Measurements taken at approximately 90 cm above soil line).

- *Size*.—Diameter approximately 6.5 cm.
- *Texture*.—Medium shaggy, increasing with age.
- *Color*.—About Light Brownish Grey 201B.
- *Lenticels*.—Present.
- *Lenticels density*.—Plentiful, about 50/cm$^2$.
- *Lenticels color*.—About Moderate Olive Brown 199A.
- *Lenticels dimensions*.—Length: approximately 4.5 mm. Width: approximately 2 mm.

One year old shoots: (Data taken in March by end of bloom).

- *Size*.—Medium, diameter approximately 5 mm.
- *Topside color*.—About Pinkish Grey 201D.
- *Underside color*.—About Light Brownish Grey 201A.
- *Internode length*.—Approximately 2 cm to 3 cm.
- *Lenticels color*.—About Pinkish Grey 201D.
- *Lenticels size*.—About 0.2 mm in diameter.
- *Presence of anthocyanin coloration*.—Absent or very sparse.
- *Density of flower buds*.—Dense to very dense.

Vegetative buds: (Data taken in September at mid-point of current season growth).

- *Size*.—Medium, approximately 2.5 mm wide×1.5 mm long.
- *Shape*.—Conical.
- *Bud shape at apex*.—Obtuse.
- *Color*.—About Pinkish Grey 201D.

Flower buds: (Data taken in September at mid-point of current season growth).

- *Shape*.—Ovoid.
- *Dimensions*.—Approximately 3.5 mm wide×4.5 mm long.
- *Color*.—About Dark Greyish Yellowish Brown N200A.
- *Ratio of flowering buds to vegetative buds*.—10 flower buds to 1 vegetative bud.

FOLIAGE

Leaves: (Data taken in March by the end of bloom).

- *Average length*.—Short to medium; approximately 60 mm without petiole.
- *Average width*.—Medium; approximately 21 mm.
- *Length/width ratio*.—Moderately elongated; about 3:1.
- *Shape*.—Elliptic.
- *Color*.—
- *Upper surface*.—About Strong Yellow Green 143B.
- *Lower surface*.—About Strong Yellow Green 143C.
- *Angle at apex (excluding tip)*.—Acute, small.
- *Angle of base*.—Acute.
- *Vein color*.—About Strong Yellow Green 143B.
- *Presence of red coloration of mid-vein on the lower side*.—Absent or very sparse.
- *Venation*.—Pinnate.
- *Surface texture*.—Smooth on both upper and lower surfaces.
- *Shape in the cross section*.—Flat.
- *Leaf blade tip*.—Curved downwardly.
- *Undulation of margin*.—Slight.
- *Margin*.—Shallow serrate.

Petiole:

- *Average length*.—Medium, approximately 9 mm.
- *Average diameter*.—Approximately 1.5 mm.
- *Color*.—About Strong Yellow Green 143B.

Stipules:

- *Number/leaf bud*.—Approximately 2 to 3.
- *Typical length*.—Short, approximately 5 mm.
- *Color*.—About Strong Yellow Green 143B.
- *Persistence*.—Falls off.

Leaf glands:

- *Average number and arrangement*.—2, alternating. Predominately on petiole side of the leaf base.
- *Form*.—Globose.
- *Dimensions*.—Approximately 0.5 mm long and 0.5 mm wide.
- *Color*.—About Strong Yellow Green 143B.

FLOWERS

General:

- *Time of beginning of leaf bud burst*.—Early, with bloom, around balloon stage, February 3$^{rd}$.

*Time of beginning of flowering*.—Early for the San Joaquin Valley, California.
*Flower blooming period*.—First bloom: Approximately February 22nd in Wasco, California. Full bloom: Approximately February 26th in Wasco, California.
*Location of first bloom*.—Tips of one year old shoots.
*Location of full bloom*.—Central part of the tree canopy.
*Duration of bloom*.—Approximately 10 days.
*Flower diameter*.—Approximately 15 mm.
*Flower form*.—Showy.
*Flower aroma*.—Slight.

Pedicels:
*Length*.—Approximately 6 mm.
*Diameter*.—Approximately 1.5 mm.
*Color*.—About Strong Yellow Green 144B.

Petals:
*Number*.—5.
*Arrangement*.—Touching.
*Color*.—About Pinkish White NN155C.
*Length*.—Approximately 9 mm.
*Width*.—Approximately 7 mm.
*Shape*.—Medium elliptic.
*Apex shape*.—Rounded.
*Base shape*.—Narrows at point of attachment.
*Surface texture*.—Smooth.
*Undulation of margins*.—Medium.
*Frequency of flowers with double petals*.—Never.
*Claw*.—Partially developed.

Sepals:
*Number*.—5.
*Length*.—Approximately 2 mm.
*Width*.—Approximately 1.5 mm.
*Shape*.—Medium ovate.
*Color*.—About Strong Yellow Green 144B.
*Surface texture*.—Smooth to slightly rough.
*Positioning*.—Adpressed to petals.

Stamens:
*Number*.—About 35.
*Average length*.—Approximately 5.5 mm.
*Filament color*.—About Pinkish White NN155C.
*Anthers pollen*.—Present.
*Flower pollen color*.—About Vivid Yellow 14A.
*Position compared to petals*.—At same level.

Pistil:
*Average length*.—Approximately 6 mm.
*Ovary diameter*.—Approximately 1.5 mm.
*Stigma position compared to anthers*.—Below.
*Frequency of supplemental pistils*.—Few.

Ovary:
*Pubescence*.—Absent.

Receptical:
*Depth*.—Medium, approximately 1.5 mm.
*Pubescence of inner surface*.—Absent.
*Pubescence of outer surface*.—Absent.

FRUIT

General: (Description taken at firm-mature near Wasco, Kern County, California).

Ripening:
*Time of beginning of fruit ripening*.—Early.
*Date of first pick*.—Approximately June 11.
*Date of last pick*.—Approximately June 20.

Size:
*Height*.—Tall, approximately 60 mm.
*Diameter in ventral side, facing suture*.—Approximately 73 mm.
*Diameter perpendicular to suture plane*.—Broad, approximately 73 mm.
*Average weight*.—Very large, approximately 165 gm.

Peduncle:
*Length*.—Approximately 11 mm.
*Width*.—Approximately 2 mm.
*Color*.—About Strong Yellow Green 141D.

Shape:
*Viewed from apex*.—Circular.
*Ventral side, facing suture*.—Broad oblate.
*Lateral view, perpendicular to suture*.—Oblate.
*Symmetry viewed from pistil end*.—Symmetric.
*Shape of pistil end*.—Flat.
*Mucron tip at pistil end*.—Absent.

Fruit stem cavity:
*Depth of stalk cavity*.—Deep, approximately 10 mm.
*Width of stalk cavity*.—Medium, approximately 8 mm.
*Prominence of suture*.—Weak.

Fruit skin:
*Thickness*.—Thin, typical of most varieties.
*Taste*.—Excellent.
*Adherence to flesh*.—Strong.
*Surface texture*.—Rippled.
*Pubescence*.—Absent.
*Glossiness*.—Strong.
*Ground color*.—Not visible.
*Overcolor*.—About Black 203B.
*Relative area of overcolor*.—Very large, about 90%.
*Pattern of overcolor*.—Solid flush.
*Tendency to crack*.—None.
*Conspicuousness of lenticels*.—Medium.

Flesh at firm-mature:
*Ripens*.—Evenly.
*Color*.—About Deep Red 60A.
*Anthocyanin coloration of flesh in central part of flesh*.—Strong.
*Anthocyanin coloration of flesh around stone*.—Weak.
*Flavor*.—Sweet-mild.
*Firmness*.—Firm; typically 10 lb pressure at harvest.
*Juice*.—Excellent.
*Acidity*.—Medium for plums.
*Sweetness*.—Medium; about 17% Brix at harvest.
*Flesh type*.—Slow melting.
*Amount of fiber*.—Weak.

Stone:
*Stone freeness*.—Cling.
*Stone size*.—Size: Large Length: Approximately 30 mm. Diameter facing suture: Approximately 15 mm. Diameter perpendicular to suture plane: Approximately 25 mm.
*Color*.—About Strong Orange Yellow 163C.
*Anthocyanin color*.—Absent.
*Intensity of brown color*.—Light.
*Position of maximum diameter*.—Middle.
*Shape from lateral view perpendicular to suture*.—Circular.
*Shape from ventral view facing suture*.—Narrow elliptic.
*Shape from basal view*.—Narrow elliptic.
*Shape in basal view*.—Medium elliptic.
*Base shape*.—Nearly straight.

*Apex shape*.—Slight point at tip.
*Stone ridges*.—Rounded throughout.
*Stone outgrowing keel*.—Well developed.
*Fibers*.—Not visible.
*Symmetry in lateral view*.—Strongly asymmetrical.
*Relief of surface*.—Predominately grooves.
*Width of stalk-end*.—Narrow.
*Tendency to split*.—Very low.
*Adherence to flesh*.—Present.
*Degree of adherence to flesh*.—Strong.

What is claimed is:

1. A new and distinct variety of plum tree named 'SUPLUM65' as described and illustrated herein.

* * * * *

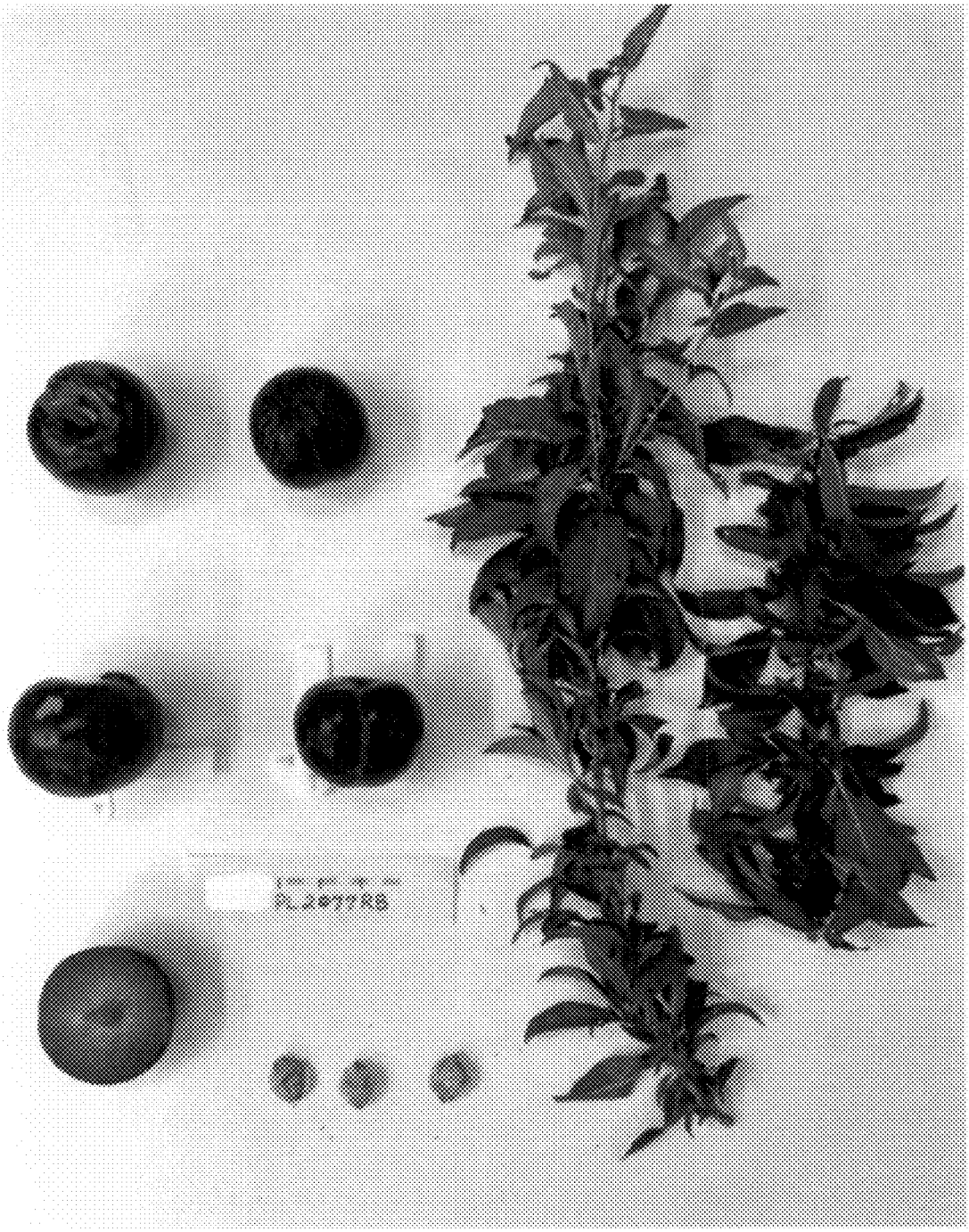
SL 267788